United States Patent [19]
DesMarais et al.

[11] Patent Number: 5,292,777
[45] Date of Patent: Mar. 8, 1994

[54] METHOD FOR HYDROPHILIZING ABSORBENT FOAM MATERIALS USING SORBITAN MONOLAURATE

[75] Inventors: Thomas A. DesMarais, Norwood; Keith J. Stone, Fairfield, both of Ohio

[73] Assignee: The Procter & Gamble Company, Cincinnati, Ohio

[21] Appl. No.: 55,419

[22] Filed: Apr. 30, 1993

Related U.S. Application Data

[63] Continuation of Ser. No. 743,838, Aug. 12, 1991, abandoned.

[51] Int. Cl.$^5$ ................................ C08J 9/28
[52] U.S. Cl. ........................ 521/64; 521/62; 521/63
[58] Field of Search ........................ 521/62, 63, 64

[56] References Cited

U.S. PATENT DOCUMENTS

| | | | |
|---|---|---|---|
| 3,255,127 | 6/1966 | von Bonin | 260/2.5 |
| 3,734,867 | 5/1973 | Will | 260/2.5 |
| 3,763,056 | 10/1973 | Will | 260/2.5 L |
| 3,806,474 | 4/1974 | Blair | 260/2.5 |
| 3,915,726 | 10/1975 | Hansen et al. | 521/64 |
| 3,992,333 | 11/1976 | Emmons et al. | 521/65 |
| 4,432,920 | 2/1984 | Ishikawa et al. | 521/61 |
| 4,473,611 | 9/1984 | Haq | 428/198 |
| 4,522,953 | 6/1985 | Barby et al. | 521/64 |
| 4,606,958 | 8/1986 | Haq et al. | 428/68 |
| 4,611,014 | 9/1986 | Jomes et al. | 521/146 |
| 4,612,334 | 9/1986 | Jones et al. | 521/146 |
| 4,668,709 | 5/1987 | Jones et al. | 521/146 |
| 4,788,225 | 11/1988 | Edwards et al. | 521/147 |
| 4,797,310 | 1/1989 | Barby et al. | 428/71 |

FOREIGN PATENT DOCUMENTS

| | | | |
|---|---|---|---|
| 0299762 | 1/1989 | European Pat. Off. | C08F 2/32 |
| 53-62138 | 6/1978 | Japan . | |
| 61-72003 | 4/1986 | Japan . | |
| 8400015 | 5/1984 | PCT Int'l Appl. . | |

*Primary Examiner*—Morton Foelak
*Attorney, Agent, or Firm*—Eric W. Guttag

[57] ABSTRACT

Normally hydrophobic foams, such as polyurethane foams and polymerized water-in-oil emulsion foams, are rendered hydrophilic by means of treatment with sorbitan monolaurate. Thus, a polymeric foam can be prepared or treated with sorbitan monolaurate and thereafter dried to leave a substantially uniformly distributed residue of sorbitan monolaurate on the internal foam surfaces. The resulting treated foams are rendered hydrophilic and are thus suitable for use in absorbent devices, including diapers, sanitary napkins, bandages, and the like.

5 Claims, 2 Drawing Sheets

0 10u

METHOD FOR HYDROPHILIZING ABSORBENT FOAM MATERIALS USING SORBITAN MONOLAURATE

This is a continuation of application Ser. No. 07/743,838, filed on Aug. 12, 1991, now abandoned.

FIELD OF THE INVENTION

The present invention relates to a method for converting normally hydrophobic polymeric foams into hydrophilic foams. The foams thus "hydrophilized" are suitable for use in absorbent devices such as diapers, adult incontinence garments, sanitary napkins, bandages, and the like, which are especially adapted for absorbing various aqueous bodily fluids.

BACKGROUND OF THE INVENTION

A wide variety of foam materials, or common "sponges", which effectively absorb moisture are well-known in commercial practice. Typically, such foams are open-cell structures and comprise various cellulosic or polymeric materials. For example, various polyurethanes and like materials have long been used to prepare synthetic foams. As is known in the art, foam materials function most efficiently as absorbents for aqueous liquids when their surfaces are substantially hydrophilic. However, many synthetic foams are prepared by the polymerization of organic monomers which yield polymeric foams which are substantially hydrophobic in nature. Accordingly, considerable attention has been given to finding means whereby otherwise hydrophobic synthetic foams can be rendered hydrophilic.

For example, it is known that some types of foams have been prepared using certain selected monomers which, themselves, impart at least some degree of hydrophilic character to the resulting polymerized foam. Such monomers are then incorporated into the basic structure of the foam network during the polymerization process. Unfortunately, the hydrophilic substituents present in the monomers can undesirably modify the basic characteristics of the resulting foam. Thus, while the resulting foam may have the desired hydrophilic character, it may lose some of its other desirable structural features or performance qualities. Moreover, such specialized, hydrophilic monomers can be expensive relative to standard monomers used to prepare foams, and thus their use can increase the overall cost of the foam.

In other processes, some foams have been treated to provide anionic substituent groups such as carboxylate or sulfonate moieties on their polymeric structures. Such anionic substituents can be effective in hydrophilizing the surface of the foams, but, unfortunately, their utilization can result in foams that are rather stiff and lack resilience. Such foams are not optimally comfortable when used in close contact with human skin, as, for example, in diapers and sanitary articles.

In some instances, synthetic hydrophobic foams can be rendered hydrophilic by incorporating small quantities of surfactants into the foam matrix. While this can render a foam hydrophilic and quite useful for some purposes, surfactant-containing foams are not always suitable for use in prolonged contact with skin, since the surfactant can cause skin irritation. In addition, some surfactants, e.g., water-soluble ones, can desorb from the foam and dissolve into the fluid being absorbed by the foam. This can significantly change the surface tension of the fluid and dramatically affect the strength with which it is held by the foam.

The manufacture of hydrophilic foams for use as fluid absorbents in sanitary articles, especially disposable diapers and sanitary napkins, requires that the foams not only have superior fluid-handling properties, but also be comfortable to the wearer and safe when used in close proximity to human skin over prolonged periods of wear. Moreover, it is important to the performance of foams designed for use in diapers and catamenials that the fluidity properties of body fluids such as urine and menses not be substantially affected by the hydrophilizing agent, such as could happen when some surfactants, e.g., water-soluble ones, are used to hydrophilize absorbent foams. Accordingly, safe, effective, economical means for hydrophilizing absorbent foams is of substantial interest to the manufacturer of such items. The present invention provides a safe and effective foam hydrophilization method which meets the foregoing requirements.

BACKGROUND ART

Lindquist; U.S. Pat. No. 3,563,243; Issued Feb. 16, 1971 relates to the use of oxyalkylene-substituted polyurethane foams in diapers. See also Kao; Japanese Patent Application 02-239863; Laid Open Sep. 21, 1990.

Jones et al; U.S. Pat. No. 4,612,334; Issued Sep. 16, 1986 and Haq et al; U.S. Pat. No. 4,606,958; Issued Aug. 19, 1986 both relate to certain foams having carboxy and other anionic substituent groups.

Kelly et al; U.S. Pat. No. 4,985,467; Issued Jan. 15, 1991 discloses a hydrophilic polyurethane foam comprising superabsorbent material. This patent also cites the following references relating to absorbent foams and/or other absorbent materials: U.S. Pat. Nos. 4,104,435; 4,717,738 4,725,629; 4,076,663; 4,454,268; 4,337,181; 4,133,784; 3,669,103; 4,464,428; 4,394,930; 3,900,030; 4,239,043; 4,731,391 and Japanese 55-168104 (1982); 57-92032 (1982); also U.S. Pat. Nos. 3,021,290; 3,171,820; 3,175,025; 4,359,558; and 4,521,544.

Barby et al; U.S. Pat. No. 4,797,310; Issued Jan. 10, 1989; Edwards et al; U.S. Pat. No. 4,788,225; Issued Nov. 29, 1988 and Barby et al; U.S. Pat. No. 4,522,953; Issued Jun. 11, 1985 all relate to porous polymeric materials (foams), some of which contain surfactants and which presumably are hydrophilic.

SUMMARY OF THE INVENTION

The present invention provides a method for rendering substantially hydrophobic polymeric foams suitable for absorbing hydrophilic liquids. Such a method comprises incorporating into a polymeric foam which is substantially hydrophobic in the absence of added or residual hydrophilizing agents, a hydrophilizing agent which is a certain type of substantially water-insoluble, mild, relatively non-irritating surfactant. The surfactant employed is one which comprises sorbitan monolaurate. It is incorporated within the foam material in a manner which leaves therein a substantially uniformly distributed, hydrophilizing amount of the sorbitan monolaurate material.

The present invention is also directed to hydrophilized polymeric foam materials themselves which are suitable for absorbing hydrophilic liquids. Such foams have the above mentioned sorbitan monolaurate-based hydrophilizing agent incorporated therein in substantially uniformly distributed, hydrophilizing amounts comprising at least about 0.05% by weight of the foam.

Such foams furthermore contain no more than about 50% by weight of the foam of free water.

DETAILED DESCRIPTION OF THE INVENTION

Figure 1:
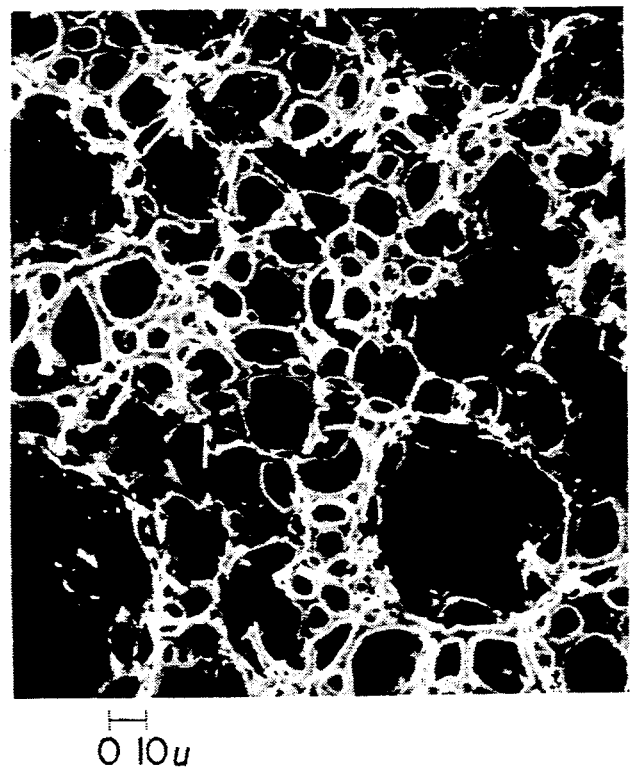
FIG. 1 of the drawings is a photomicrograph of the interstices of a typical hydrophilizable absorbent foam of the present invention.

The hydrophilization method of the present invention deals with the treatment of polymeric foam materials which are suitable for absorbing liquids into their foam structures. Polymeric foams can in general be characterized as the structures which result when a relatively monomer-free gas or relatively monomer-free liquid is dispersed as bubbles in a polymerizable monomer-containing liquid, followed by polymerization of the polymerizable monomers in the monomer-containing liquid which surrounds the bubbles. The resulting polymerized dispersion can be in the form of a porous solidified structure which is an aggregate of cells, the boundaries or walls of which cells comprise solid polymerized material. The cells themselves contain the relatively monomer-free gas or relatively monomer-free liquid which, prior to polymerization, had formed the "bubbles" in the liquid dispersion.

As described more fully hereafter, preferred polymeric foam materials useful in the present invention are those prepared by polymerizing a particular type of water-in-oil emulsion. Such an emulsion is formed from a relatively small amount of a polymerizable monomer-containing oil phase and a relatively larger amount of a relatively monomer-free water phase. The relatively monomer-free, discontinuous "internal" water phase thus forms the dispersed "bubbles" surrounded by the continuous polymerizable monomer-containing oil phase. Subsequent polymerization of the monomers in the continuous oil phase forms the cellular foam structure. The aqueous liquid remaining in the foam structure formed upon polymerization can be removed by pressing and/or drying the foam.

Highly preferred polymeric foam materials for use in the present invention are those prepared by polymerizing water-in-oil emulsions containing certain polymerizable monomers, such as styrene, alkyl(meth)acrylates and/or divinylbenzene, in the oil phase of such emulsions. The most preferred polymeric foam materials of this type are those described in the concurrently filed patent application of DesMarais, Stone, Thompson, Young, LaVon, and Dyer having U.S. Ser. No. 07/743,839, entitled "Absorbent Foam Materials for Aqueous Body Fluids and Absorbent Articles Containing Such Materials," which application is incorporated herein by reference. Such highly preferred foam materials will generally have a pore volume of from about 12 to 100 ml/g and a capillary suction specific surface area of from about 0.5 to 5.0 $M^2/g$. These foams can be prepared from water-in-oil emulsions wherein the water to oil weight ratio ranges from about 12:1 to 100:1, more preferably from about 20:1 to 70:1.

Another common type of polymeric foam material useful in the present invention comprises the polyurethanes. Polyurethane foams are those prepared by reacting a polyisocyanate such as a diisocyanate with a hydroxyl-containing material such as a polyether polyol in the presence of water and a catalyst. As the polymer forms, the water reacts with the isocyanate groups to cause cross-linking. Carbon dioxide is also produced, and this causes foaming. Trifluoromethane or other volatile materials may also be employed as a blowing agent.

Polymeric foams, including the preferred foams herein prepared from polymerizable water-in-oil emulsions, may be relatively closed-celled or relatively open-celled in character, depending upon whether and/or the extent to which, the cell walls or boundaries, i.e., the cell windows, are filled or taken up with polymeric material. The polymeric foam materials useful in the method of the present invention are those which are relatively open-celled in that the individual cells of the foam are for the most part not completely isolated from each other by polymeric material of the cell walls. Thus the cells in such substantially open-celled foam structures have intercellular openings or "windows" which are large enough to permit ready fluid transfer from one cell to the other within the foam structure.

In substantially open-celled structures of the type useful herein, the foam will generally have a reticulated character with the individual cells being defined by a plurality of mutually connected, three dimensionally branched webs. The strands of polymeric material which make up the branched webs of the open-cell foam structure can be referred to as "struts." Open-celled foams having a typical strut-type structure are shown by way of example in the photomicrograph set forth as FIG. 1. For purposes of the present invention, a foam material is "open-celled" if at least 80% of the cells in the foam structure are in fluid communication with at least one adjacent cell.

The polymeric materials that form the foams which are used as the starting materials in the method of this invention will generally be non-swellable in aqueous liquids and will also generally be substantially free of polar functional groups on their polymer structures. Thus after the structures of such foams have been formed, the foam structure surfaces comprise polymeric materials which, in the absence of any residual or added surfactants or other hydrophilizing agents, would be substantially hydrophobic in character.

The extent to which polymeric foam materials are either "hydrophobic" or "hydrophilic" can be quantified by referencing the "adhesion tension" exhibited by such foams in contact with an absorbable test liquid. Adhesion tension is defined by the formula $$AT = \gamma \cos \theta$$

wherein
- AT is adhesion tension in dynes/cm;
- $\gamma$ is the surface tension of a test liquid absorbed by the foam material in dynes/cm;
- $\theta$ is the contact angle in degrees between the surface of foam polymer material and the vector which is tangent to the test liquid at the point that the test liquid contacts the foam polymer surface.

For any given foam material, the adhesion tension exhibited by the foam can be determined experimentally using a procedure whereby weight uptake of a hydrophilic test liquid, e.g., synthetic urine, is measured for a foam sample of known dimensions and capillary suction specific surface area. Such a procedure is described in greater detail in the TEST METHODS section hereinafter.

For purposes of the present invention, a particular foam material is considered to be substantially hydrophobic if, in the substantial absence of any added or residual surfactants or other hydrophilizing agents, it exhibits an adhesion tension of less than about 15 dynes/cm as determined by capillary suction uptake of synthetic urine having a surface tension of 65±5 dynes/cm. Conversely, a polymeric foam material is considered to be relatively hydrophilic when it exhibits an adhesion tension of 15 dynes/cm or greater, preferably 20 dynes/cm or greater, as determined by capillary suction uptake of this same synthetic urine.

In accordance with the foam hydrophilization method herein, a substantially hydrophobic polymeric foam is treated so as to incorporate into the foam material a hydrophilizing agent which comprises a certain type of substantially water-insoluble, mild, relatively non-irritating surfactant which tends to enhance the wettability of the polymeric surfaces with which it is contacted and onto which it may be deposited. The selected surfactant of this type which has been discovered to be an especially useful one for imparting desirable hydrophilicity characteristics to open cell polymeric absorbent foams is sorbitan monolaurate. Sorbitan monolaurate is a partial ester formed by reacting sorbitol or its anhydrides with a source of lauric acid. Sorbitan monolaurate is a know emulsifier which is substantially insoluble in water. It is commercially marketed under the tradename SPAN®20 and is available in the form of an amber liquid.

The sorbitan monolaurate-based surfactant useful as a hydrophilizing agent can be incorporated into the foam materials herein by any suitable means which will result in the surfactant(s) contacting the polymeric surfaces of the foam material. Most preferably, this can be brought about by employing the sorbitan monolaurate surfactant material as a component in the process which is used to prepare the foam materials herein. For the preferred foams herein which are prepared by polymerizing water-in-oil emulsions, the substantially water-insoluble sorbitan monolaurate can be added as an emulsifier to the monomer-containing oil phase of such emulsions. In this manner, the sorbitan monolaurate surfactant performs the dual role of stabilizing the emulsions to be polymerized and acting as a residual hydrophilizing agent which contacts and preferably coats the polymeric surfaces of the foam structure after this structure is formed. Sorbitan monolaurate surfactant material can be added to the polymerizable monomer-containing oil phase to the extent of from about 0.5% to 20% by weight, more preferably from about 1% to 16% by weight, of the polymerizable monomer materials in the oil phase.

Alternatively, the sorbitan monolaurate surfactant used in the present invention can be introduced or reintroduced into foam material which contains no surfactant as made or from which residual surfactants have been removed. Such introduction or reintroduction of sorbitan monolaurate can be carried out by treating such foams with an appropriate surfactant solution or suspension. Thus, the water-insoluble sorbitan monolaurate surfactant useful herein can be dissolved or dispersed in a suitable solvent or carrier such as isopropanol, and the resulting solution or suspension can be contacted with the foam material to be treated therewith. In this manner, the sorbitan monolaurate hydrophilizing agent can be incorporated into the interstices of the foam structure. Such treatment of foam materials which are substantially hydrophobic as formed may be difficult, however, because sorbitan monolaurate-based hydrophilizing agent solutions or suspensions may not be readily absorbed into hydrophobic foams. Accordingly, it may be necessary to force sorbitan monolaurate-based hydrophilizing agent solution or suspension into the foam structure by application of pressure or by means of repeated washing and/or foam squeezing steps in order to realize acceptably uniformed distribution of the hydrophilizing agent within the foam structure.

The sorbitan monolaurate surfactant used in the present invention is generally incorporated into foam materials in amounts which, in conjunction with any other ancillary hydrophilizing agents which may be utilized, impart suitable hydrophilicity characteristics to the foams so treated. Frequently such amounts of incorporated sorbitan monolaurate surfactant will range from about 0.5% to 20% by weight of the polymerized foam material, more preferably from about 1% to 16% by weight of the polymeric foam material.

In addition to incorporating the sorbitan monolaurate surfactant material into the foam structure as hereinbefore described, it is also possible to incorporate into the foam structure additional types of materials which act as ancillary hydrophilizing agents in the foams treated therewith. The most commonly utilized ancillary hydrophilizing agents of this type include toxicologically acceptable, hydrated or hydratable calcium and magnesium salts such as calcium chloride. A method for hydrophilizing polymeric foam materials by incorporating thereinto a combination of water-insoluble surfactants (including sorbitan monolaurate) and hydrophilizing agent salts such as calcium chloride is, in fact, the subject of the concurrently filed U.S. patent application of Thomas A. DesMarais, which application has Ser. No. 07/743,951 and is incorporated herein by reference.

It will be appreciated that for the sorbitan monolaurate and any other ancillary hydrophilizing agents to be effective in imparting hydrophilicity characteristics to the foam being treated therewith, both the sorbitan monolaurate and the ancillary hydrophilizing agents must be substantially uniformly distributed within the internal structure of the foam. If the sorbitan monolaurate and the ancillary hydrophilizing agents are deposited within the foam only in discrete discontinuous zones, such as may happen for example if the sorbitan monolaurate or hydrophilizing agent treating liquids form beads or droplets within the foam structure formed by the polymeric struts, then the full foam hydrophilization effect provided by the method herein may not be realized.

Prior to their use as absorbents, foam materials which have had their polymeric surfaces rendered hydrophilic by incorporation therein of sorbitan monolaurate and optionally other ancillary hydrophilizing agents such as calcium chloride will generally need to be dried. Drying will generally be necessary to remove from such treated foams liquids, e.g., water and/or alcoholic solvents, which may have been used in the foam preparation process or employed to facilitate the incorporation of the hydrophilizing agents into the foam structure. Liquid removal may be brought about by simple compression of the foam material to squeeze out liquids. Liquid removal may also be effected by utilizing air, heat or microwave treatment methods which serve to remove liquid, but not excessive amounts of the incorporated hydrophilizing agents themselves, from the foam structure. Frequently, liquids such as solvents will be removed from the foam structures treated by the method herein such that residual solvent, e.g., free water, in the foam comprises no more than about 50% by weight of the (dry) foam, more preferably no more than about 10% by weight of the (dry) foam.

Treatment of polymeric foam materials in accordance with the method of the present invention renders such foam materials suitable for absorbing hydrophilic liquids. Accordingly, the hydrophilized foam materials of the present invention are especially useful as absorbents for aqueous body fluids in absorbent articles such as diapers, incontinence pads, catamenial products, and the like. The hydrophilic character of such treated absorbent foams permits such materials to readily accept body fluids such as urine and menses into their foam structures. Hydrophilized foam materials will in general exhibit desirable fluid transport, e.g., wicking, properties for aqueous fluids such as body fluids so that absorbed liquid can be moved within the material from one region of the absorbent foam to another.

A simple screening test useful for determining relative hydrophilicity of treated foam samples involves measurement of foam sample sink time. In such a test, foam samples are dropped into a beaker of aqueous test fluid, e.g., synthetic urine, and the amount of time taken for the samples to sink is recorded. Shorter sink times are observed for samples of greater hydrophilicity. A typical sink time test is described in greater detail hereinafter in the TEST METHODS section.

TEST METHODS

In describing the present invention, certain characteristics of absorbent foam materials are set forth. Where reported, these characteristics can be determined using the following test fluids and test methods.

I) Test Fluids and Foam Sample Preparation

A) Test Fluid—Synthetic Urine

Several of the measurements described in the tests herein involve the use of a test fluid such as synthetic urine or ethanol. The synthetic urine utilized in the tests described hereinafter is made from a commercially available synthetic urine preparation manufactured by Jayco Pharmaceuticals (Mechanicsburg, Pa., 17055). This Jayco synthetic urine made from the preparation comprises KCl, 0.2%; $Na_2SO_4$, 0.2%; $NH_4H_2PO_4$, 0.085%; $(NH_4)_2HPO_4$, 0.015%; $CaCl_2*2H_2O$, 0.025%; and $MgCl_{22}*6H_2O$, 0.05%. (weight %'s) The synthetic urine samples are prepared according to the label instructions using distilled water. To aid dissolution, the Jayco salt mixture is slowly added to the water. The sample is filtered if necessary to remove any particulates. Any unused synthetic urine is discarded after one week. To improve visibility of the fluid, 5 drops of blue food color can be added per liter of synthetic urine solution. The Jayco synthetic urine utilized has a surface tension of 65±5 dynes/cm.

B) Foam Sample Preparation

The following Adhesion Tension and Sink Time tests involve the preparation and testing of foam samples of a particular specified size. These foam samples of the requisite size should be cut from larger blocks of foam using a sharp reciprocating knife saw. Use of this or equivalent type of foam cutting device serves to substantially eliminate foam sample edge flaws which could have adverse impact on certain of the measurements made in carrying out the test procedures hereinafter set forth.

Sample size specification also includes a dimension for foam sample caliper or thickness. Caliper or thickness measurements for purposes of the present invention should be made when the foam sample is under a confining pressure of 0.05 psi (350 Pa).

II) Adhesion Tension Determination

The adhesion tension exhibited by hydrophilized foam samples which imbibe test fluids via capillary suction is the product of the surface tension, $\gamma$, of the test fluid times the cosine of the contact angle, $\theta$, exhibited by the test fluid in contact with the interior surfaces of the foam sample. Adhesion tension can be determined experimentally by measuring the equilibrium weight uptake by capillary suction exhibited by two test samples of the same foam using two different test liquids. In the first step of such a procedure, specific surface area of the foam sample is determined using ethanol as the test fluid. The specific surface area so determined is then used as one factor in experimentally determining adhesion tension by measuring capillary suction uptake of a second test fluid, synthetic urine.

A) Specific Surface Area Measurements

Capillary Suction Specific surface area of the foam absorbents employed in the invention herein can be determined from the equilibrium weight uptake of a test liquid of known low surface tension. In this instance, absolute ethanol (flash point is 10° C.) is used.

To conduct the test, a tared foam sample strip of suitable dimensions (e.g., 25 cm long×2 cm wide×0.8 cm thick) is equilibrated at 22°±2° C., is positioned vertically and at one end is immersed 1-2 mm into a reservoir of the ethanol using a lab jack. The ethanol is allowed to wick up the foam strip to its equilibrium height which should be less than the sample length. The ethanol-containing strip is then weighed while still touching the reservoir to determine the weight of total ethanol uptake. During this procedure the sample should be shielded to prevent ethanol evaporation.

Specific surface area of the foam sample can be calculated from the following formula:

$$S_c = \frac{M_e G L_n}{M_n \gamma_e}$$

where $S_c$=capillary suction specific surface area in $cm^2/gm$; $M_e$=mass of liquid uptake of EtOH in gms; G=the gravitational constant which is 980 $cm/sec^2$; $L_n$=total length of sample in cm; $M_n$=mass of dry foam sample in gm; and $\gamma_e$=surface tension of EtOH which is 22.3 dynes/cm.

B) Adhesion Tension Measurements

The capillary suction uptake procedure used as described to determine specific surface area of the foam sample is then repeated on other samples of the same foam in identical manner to the ethanol procedure except that JAYCO synthetic urine is used as the test fluid and the test is carried out at 37° C. Contact angle of the synthetic urine can then be calculated as follows from the known specific surface area and the synthetic urine uptake data:

$$\cos\theta_U = \frac{M_U G L_N}{M_N \gamma_U S_c}$$

where $\theta_U$=contact angle of Jayco synthetic urine in degrees; $M_U$=mass of liquid uptake of Jayco synthetic urine in gms; G=gravitational constant which is 980 cm/sec$^2$; $M_N$=mass of dry foam sample in gm; $\gamma_U$=surface tension of JAYCO urine which is ~65 dynes/cm; $S_c$=specific surface area of the foam sample in cm$^2$/gm as determined by the ethanol uptake procedure; and $L_n$=length of the foam sample in cm.

When a surfactant is present (for example, residual emulsifier on the foam sample surfaces and/or in the advancing test liquid), characterization of the advancing liquid front is defined by applying the adhesion tension (AT) equation:

$$AT = \frac{M_T G L_N}{M_N S_c}$$

wherein $M_T$ is the mass of the test liquid taken up by the foam sample, and G, $L_N$, $M_N$, and $S_c$ are as hereinbefore defined. [See Hodgson and Berg, *J. Coll. Int. Sci.*, 121(1), 1988, pp 22-31]

In determining adhesion tension for any given test liquid, no assumption is made of the numerical value of the surface tension at any point in time so that possible changes in surfactant concentration on the sample surfaces and/or in the advancing liquid during wicking are immaterial. The experimental value of adhesion tension ($\gamma\cos\theta$) is especially useful when viewed as a percentage of the maximum adhesion tension which is the surface tension of the test liquid (e.g., the maximum adhesion tension using JAYCO synthetic urine would be $[65\pm5][\cos 0°] = 65\pm5$ dynes/cm).

III. Sink Time Determination

Cylindrical foam samples 1.125 inches (2.86 cm) in diameter of any suitable thickness (e.g., 0.8 cm) are cut from larger foam pieces. The cylindrical samples are dropped from a height of 2-3 inches (5-7.6 cm) into a 250 mL beaker containing approximately 100 mL of Jayco synthetic urine in such a way that the flat cylindrical surface contacts the test fluid in the beaker. A stopwatch timer is started as soon as the bottom of the foam sample contacts the test fluid. The sample is observed until the test fluid wicks to the top surface of the sample. When the top face of the foam sample is substantially wetted out, the timer is stopped, and the sink time is recorded.

Temperature of the test fluid can affect sink time significantly, especially for the preferred water-in-oil based foams of the present invention. Thus the test fluid should be maintained at the same temperature for all samples being comparatively tested in a particular sink time screening exercise. Test fluid "cold" temperatures of about 70°-80° F. (21°-27° C.) and test fluid "hot" temperatures of about 110°-120° F. (43°-49° C.) are frequently employed.

EXAMPLES

Preparation of hydrophilized absorbent foam materials, the characteristics of such hydrophilized foam materials and utilization of these hydrophobic foam absorbents in a disposable diaper are all illustrated by the following examples.

EXAMPLE I

Preparation of a hydrophilized foam absorbent on a semi-pilot plant scale is illustrated by this example.

Emulsion Preparation

Calcium chloride (36.32 kg) and potassium persulfate (568 g) are dissolved in 378 liters of water. This provides the water phase stream to be used in a continuous process for forming a polymerizable High Internal Phase Emulsion (HIPE).

To a monomer combination comprising styrene (1600 g), divinylbenzene 55% technical grade (1600 g) and 2-ethylhexylacrylate (4800 g) is added sorbitan monooleate (960 g as SPAN ® 20). After mixing, this combination of materials is allowed to settle overnight. The supernatant is withdrawn and used as the oil phase in a continuous process for forming a polymerizable HIPE emulsion. (About 75 g of a sticky residue is discarded.)

At an aqueous phase temperature of 48° C. to 50° C., and an oil phase temperature of 22° C., separate streams of the oil phase and water phase are fed to a dynamic mixing apparatus. Thorough mixing of the combined streams in the dynamic mixing apparatus is achieved by means of a pin impeller. At this scale of operation, an appropriate pin impeller comprises a cylindrical shaft of about 21.6 cm. in length with a diameter of about 1.9 cm. The shaft, as described in Example I, holds 4 rows of pins, 2 rows having 17 pins and 2 rows having 16 pins, each having a diameter of 0.5 cm. extending outwardly from the central axis of the shaft to a length of 1.6 cm. The pin impeller is mounted in a cylindrical sleeve which forms the dynamic mixing apparatus, and the pins have a clearance of 0.8 mm from the walls of the cylindrical sleeve.

A spiral static mixer is mounted downstream from the dynamic mixing apparatus to provide some back pressure in the dynamic mixing and to provide improved incorporation of components into the emulsion that is eventually formed. Such a static mixer is 14 inches (35.6 cm) long with a 0.5 inch (1.3 cm) outside diameter. The static mixer is a TAH Industries Model 070-821, modified by cutting off 2.4 inches (6.1 cm).

The combined mixing apparatus set-up is filled with oil phase and water phase at a ratio of 2 parts water to 1 part oil. The dynamic mixing apparatus is vented to allow air to escape while filling the apparatus completely. The flow rates during filling are 1.127 g/sec oil phase and 2.19 cm$^3$/sec water phase.

Once the apparatus set-up is filled, agitation is begun in the dynamic mixer, with the impeller turning at 1800 RPM. The flow rate of the water phase is then steadily increased to a rate of 35.56 cm$^3$/sec over a time period of 130 sec. The back pressure created by the dynamic and static mixers at this point is 7.5 PSI (51.75 kPa). The impeller speed is then steadily decreased to a speed of 1200 RPM over a period of 60 sec. The back pressure drops to 4.5 PSI (31.05 kPa). At this point, the impeller speed is instantly increased to 1800 RPM. The system back pressure remains constant thereafter at 4.5 PSI (31.05 kPa).

Polymerization of the Emulsion

The formed emulsion flowing from the static mixer at this point is collected in Rubbermaid Economy Cold Food Storage Boxes, Model 3500. These boxes are constructed of food grade polyethylene and have nominal dimensions of 18"×26"×9" (45.7 cm×66 cm 22.9 cm).

The true inside dimensions of these boxes are 15"×23"×9" (38.1 cm×58.4 cm×22.9 cm). These boxes are pretreated with a film of a solution comprising a 20% solution of SPAN ® 20 in an equal weight solvent mixture of xylene and isopropanol. The solvent mixture is allowed to evaporate to leave only the SPAN ® 20. Forty-seven liters of emulsion are collected in each box.

The emulsion-containing boxes are kept in a room maintained at 65° C. for 18 hours to bring about polymerization of the emulsion in the boxes to thereby form polymeric foam material.

Foam Washing, Hydrophilization and Dewatering

After curing is complete, the wet cured foam material is removed from the curing boxes. The foam at this point contains about 30-40 times the weight of polymerized material (30-40×) of the residual water phase containing dissolved emulsifiers, electrolyte and initiator. The foam material is sliced with a sharp reciprocating saw blade into sheets which are 0.350 inches (0.89 cm) in caliper. These sheets are then subjected to compression in a series of 3 nip rolls which gradually reduce the residual water phase content of the foam to about 6 times (6×) the weight of the polymerized material. At this point, the sheets are then resaturated with a 1% CaCl$_2$ solution at 60° C., are squeezed in a nip to a water phase content of about 10×, resaturated with the 1% CaCl$_2$ solution at 60° C., and then squeezed again in a nip to a water phase content of about 10×.

The foam sheets, which now contain about 10× of what is essentially a 1% CaCl$_2$ solution are passed through a final nip equipped with a vacuum slot. The last nip reduces the CaCl$_2$ solution content to about 5 times (5×) the weight of polymer. The foam remains compressed after the final nip at a caliper of about 0.080 in. (0.2 cm). The foam is then dried in an air circulating oven set at about 60° C. for about three hours. Such drying reduces the moisture content to about 5-7% by weight of polymerized material. At this point, the foam sheets have a caliper of about 0.075 in. (0.19 cm) and are very drapeable. The foam also contains about 5% by weight (anhydrous basis) of residual hydrated calcium chloride as a hydrophilizing agent along with about 11% of residual sorbitan monolaurate (SML). In the collapsed state, the density of the foam is about 0.17 g/cm$^3$. When expanded to its free absorbent capacity (26.5 ml/g) in JAYCO synthetic urine, the expanded foam has a capillary suction specific surface area of about 2.24 m$^2$/g, a pore volume of about 29.5 cc/g and an average cell size of about 15 microns.

The SML/CaCl$_2$-hydrophilized foam sheets prepared as in Example II represent a preferred "thin-until-wet" embodiment of the present invention inasmuch as these hydrophilized foam sheets are in the form of collapsed foam material which will expand upon contact with aqueous body fluids. Once expanded, the foam materials are useful for absorbing the body fluids that have caused the foam to expand. Such preferred collapsed foams are those which are formed from a non-hydrolyzed polymeric material, which have a capillary suction specific surface area of from about 0.5 to 5.0 m$^2$/g, which contain from about 0.5% to 20% of residual sorbitan monolaurate, and which contain from about 0.1% to 7% by weight (anhydrous basis) of the foam material of a toxicologically acceptable, hygroscopic, hydrated salt, which is preferably calcium chloride or magnesium chloride, as an ancillary hydrophilizing agent.

In its collapsed state, such hydrophilized foam material will have a residual water content of from about 4% to 15% by weight of polymerized material when it is stored at ambient conditions of 72° F. (22° C.) and 50% relative humidity. This water content includes both water of hydration associated with the hygroscopic, hydrated salt as well as free water absorbed within the foam. Such collapsed hydrophilized foam material will also have a dry basis density ranging from about 0.08 to 0.3 g/cm$^3$.

In its expanded state, such preferred thin-until-wet SML/CaCL$_2$-hydrophilized foam materials will have a pore volume from about 12 to 100 ml/g and will exhibit a resistance to compression deflection such that a confining pressure of 5.1 kPa produces after 15 minutes of strain from about 5% to 95% compression of the structure when it is saturated at 37° C. to its free absorbent capacity with synthetic urine having a surface tension of 65±5 dynes/cm. The average cell size of these preferred thin-until-wet hydrophilized foam materials in the expanded state will range from about 5 to 30 microns. The dry basis density of the expanded hydrophilized foam material upon saturation to its free absorbent capacity in this synthetic urine will range from about 9% to 28% of its dry basis density in the collapsed state.

EXAMPLE II

Both a foam material prepared in general as in Example I and a conventional polyurethane foam (SIF-100) are tested for their hydrophilicity characteristics using the Sink Time procedure described in the TEST METHODS section. Such foam materials are also subjected to various treatment procedures to remove added or residual hydrophilizing agents therefrom and to selectively reintroduce certain materials to test their effectiveness at imparting hydrophilicity characteristics to the foam materials.

The foam materials, treating agents and sink time test results are set forth hereinafter in Table I.

TABLE I

|  | CaCl$_2$ wt % | SML[1] wt % | Sink Time in JAYCO Synthetic Urine | |
| --- | --- | --- | --- | --- |
|  |  |  | Cold (~21-27° C.) | Hot (~43-49° C.) |
| EXAMPLE I TYPE FOAM |  |  |  |  |
| As-made | 3.7% | 11% | 70 sec | 3 sec |
| Water washed |  |  |  |  |
| -Expanded Form | 0 | 11% | >20 min | 4 sec |
| -Collapsed Form | 0 | 11% | 300 sec | 2 sec |
| -CaCl$_2$ re-treated (from H$_2$O) | 3.6% | 11% | 180 sec | 3 sec |
| IPA[2] washed | 0 | 0 | *Floated indefinitely* | |
| -CaCl$_2$ re-treated (from IPA) | ~5% | 0 | Floated for hrs | Floated >15 min |
| -SML re-treated (from IPA) | 0 | 11% | ~5 sec | ~1 sec |

TABLE I-continued

| | CaCl$_2$ wt % | SML[1] wt % | Sink Time in JAYCO Synthetic Urine | |
|---|---|---|---|---|
| | | | Cold (~21-27° C.) | Hot (~43-49° C.) |
| -SMO/STO[3] re-treated (from IPA) | 0 | 19% | ~300 sec | ~180 sec |
| POLYURETHANE FOAM (SIF-100) | | | | |
| As-made | 0 | 0 | Floated | Sank very slowly |
| SML treated (from IPA) | 0 | 16% | 1 sec | 1 sec |

[1]SML = Sorbitan monolaurate (SPAN ® 20)
[2]IPA = Isopropanol
[3]SMO/STO = Sorbitan monooleate (SPAN ® 80) and sorbitan trioleate (SPAN ® 85) in a 4:1 weight ratio The Table I data show that both sorbitan monolaurate and the combination of CaCl$_2$ and sorbitan monolaurate incorporated into foam samples of the Example I type provide foams having hydrophilicity characteristics which are in general superior to those having either no incorporated hydrophilizing agents at all or CaCl$_2$ or other similar sorbitan ester surfactants alone. The Table I data further show that incorporation of sorbitan monolaurate into a polyurethane foam also imparts desirable hydrophilicity characteristics to a foam of that type.

EXAMPLE III

Figure 2:
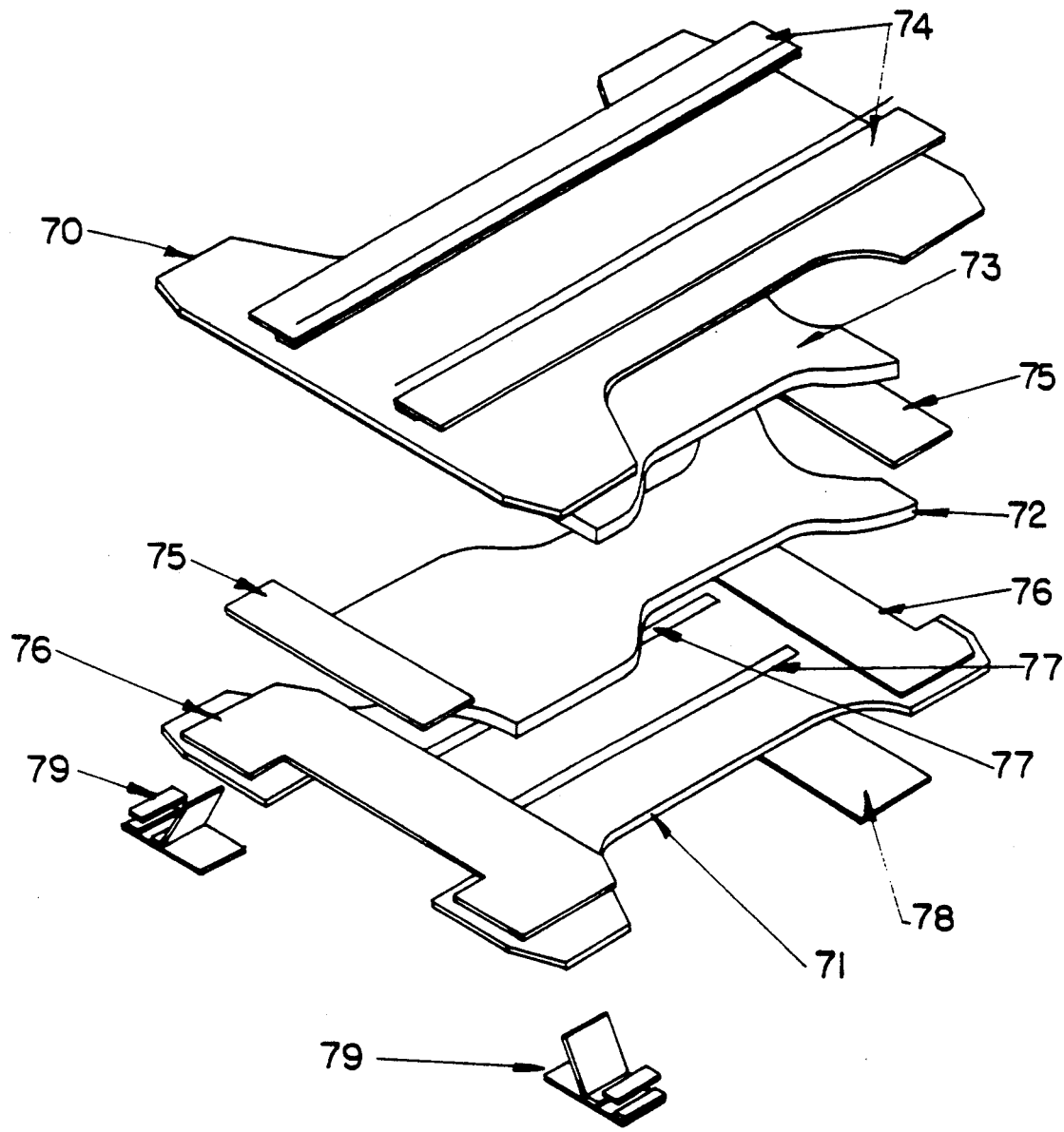
FIG. 2 of the drawings represents a blown-apart view of the components of a diaper structure which has a dual layer absorbent core configuration and which employs a hydrophilized absorbent foam material as one of its elements.

A disposable baby diaper using a foam absorbent which has been hydrophilized according to this invention is prepared as follows using the configuration and components shown in the expanded and blown-apart depiction of FIG. 2. Such a diaper comprises a thermally bonded polypropylene topsheet, 70, a fluid-impervious polyethylene backing sheet, 71, and a dual layer absorbent core positioned between the topsheet and the backing sheet. The dual layer absorbent core comprises a modified hourglass-shaped, fluid storage/redistribution layer, 72, comprising a hydrophilized absorbent foam of the Example I type positioned below a modified-hourglass shaped fluid acquisition/distribution layer, 73. The topsheet contains two substantially parallel barrier leg cuff strips, 74, with elastic. Affixed to the diaper backsheet are two rectangular elasticized waistband members, 75. Also affixed to each end of the polyethylene backsheet are two waistshield elements, 76, constructed of polyethylene. Also affixed to the backsheet are two parallel leg elastic strips, 77. A sheet of polyethylene, 78, is affixed to the outside of the backsheet as a dedicated fastening surface for two pieces, 79, of Y type which can be used to fasten the diaper around the wearer.

The acquisition/distribution layer of the diaper core comprises a 92%/8% wetlaid mixture of stiffened, twisted, curled cellulosic fibers and conventional non-stiffened cellulosic fibers. The stiffened, twisted, curled cellulosic fibers are made from southern softwood kraft pulp (Foley fluff) which has been crosslinked with glutaraldehyde to the extent of about 2.5 mole percent on a dry fiber cellulose anhydroglucose basis. The fibers are crosslinked according to the "dry crosslinking process" as described in Dean, Moore, Owens and Schoggen; U.S. Pat. No. 4,822,453; Issued Apr. 18, 1989, incorporated herein by reference.

These stiffened fibers are similar to the fibers having the characteristics described as follows in Table II.

Table II

Stiffened, Twisted, Curled Cellulose (STCC) Fibers

Type = Southern softwood kraft pulp crosslinked with glutaraldehyde to the extent of 1.41 mole percent on a dry fiber cellulose anhydroglucose basis
Twist Count Dry = 6.8 nodes/mm
Twist Count Wet = 5.1 nodes/mm
Isopropyl Alcohol Retention Value = 24%
Water Retention Value = 37%
Curl Factor = 0.63

The conventional non-stiffened cellulose fibers used in combination with the STCC fibers are also made from Foley fluff. These non-stiffened cellulose fibers are refined to about 200 CSF (Canadian Standard Freeness).

The acquisition/distribution layer has an average dry density of about 0.07 g/cm$^3$, an average density upon saturation with synthetic urine, dry weight basis, of about 0.08 g/cm$^3$, and an average basis weight of about 0.03 g/cm$^2$. About 9.2 grams of the fluid acquisition/distribution layer are used in the diaper core. The surface area of the acquisition/distribution layer is about 46.8 in$^2$ (302 cm$^2$). It has a caliper of about 0.44 cm.

The fluid storage/redistribution layer of the diaper core comprises a modified hourglass-shaped piece of a hydrophilized absorbent foam of the type described hereinbefore in Example I. About 12 grams of this foam are used to form this storage/redistribution layer which has a surface area of about 65.9 in$^2$ (425 cm$^2$) and a caliper of about 0.325 in (0.826 cm).

A diaper having this particular core configuration exhibits especially desirable and efficient utilization of the core for holding discharged urine and accordingly provides exceptionally low incidence of leakage when worn by an infant in the normal manner.

EXAMPLE IV

A lightweight pantiliner suitable for use between menstrual periods comprises a hydrophilized foam pad according to Example I (surface area 117 cm$^2$; thickness 1.5 mm), said pad being interposed between a porous formed-film topsheet according to Ahr et al; U.S. Pat. No. 4,463,045; Issued Jul. 31, 1984 and a backsheet which comprises a 0.03 mm thickness polyethylene film.

EXAMPLE V

A sanitary napkin is prepared according to Example IV, but employs a 4 mm thick hydrophilized foam pad according to Example I and a porous nonglossy formed film topsheet. The sanitary napkin has the configuration described in Van Tilburg; U.S. Pat. No. 4,687,478; Issued Aug. 18, 1987.

What is claimed is:

1. A method for preparing a hydrophilized polymeric foam material suitable for absorbing hydrophilic liquids, which method comprises:
   A) polymerizing a water-in-oil emulsion containing polymerizable monomers and from about 0.5% to 20% by weight of the polymerizable monomers of sorbitan monolaurate in the oil phase of said emulsion, to thereby form a polymeric foam material; and
   B) thereafter drying said polymeric foam material to remove water therefrom and to leave incorporated within said foam material: (1) no more than about 50% by weight of said foam material of free water; and (2) a substantially uniformly distributed, hydrophilizing amount of said sorbitan monolaurate.

2. A method according to claim 1 wherein
   A) the oil phase of the emulsion which is polymerized contains from about 1% to 16% by weight of the polymerizable monomers in the oil phase of sorbitan monolaurate; and
   B) said polymeric foam material is dried so as to contain no more than about 10% by weight of said foam material of free water.

3. A method according to claim 2 wherein the polymerizable monomers in the oil phase of the water-in-oil emulsion used to form said polymeric foam material are selected from styrene, alkyl(meth)acrylates, divinylbenzene and combinations of these monomers.

4. A method according to claim 1 wherein said polymeric foam material is an open-celled foam.

5. A method according to claim 4 wherein the amount of said sorbitan monolaurate left incorporated within said foam material comprises at least about 0.05% by weight of said foam material.

* * * * *